United States Patent [19]

Bieser

[11] 4,021,499
[45] May 3, 1977

[54] PROCESS FOR SEPARATING ETHYLBENZENE

[75] Inventor: Herbert J. Bieser, Des Plaines, Ill.

[73] Assignee: UOP Inc., Des Plaines, Ill.

[22] Filed: Nov. 5, 1975

[21] Appl. No.: 628,866

[52] U.S. Cl. .............................. 260/674 SA; 55/62
[51] Int. Cl.$^2$ .......................................... C07C 7/00
[58] Field of Search ............... 260/674 SA; 210/34; 55/62; 208/310 Z

[56] References Cited

UNITED STATES PATENTS

| | | | |
|---|---|---|---|
| 3,686,342 | 8/1972 | Neuzil | 260/674 SA |
| 3,696,107 | 10/1972 | Neuzil | 260/674 SA |
| 3,715,409 | 2/1973 | Broughton | 260/674 SA |
| 3,917,734 | 11/1975 | deRosset | 208/310 Z |

Primary Examiner—Frank A. Spear, Jr.
Assistant Examiner—E. Rollins Cross
Attorney, Agent, or Firm—James R. Hoatson, Jr.; Thomas K. McBride; William H. Page, II

[57] ABSTRACT

An improved process for separating ethylbenzene at high purity and at high recovery from a feed stream comprising ethylbenzene and paraxylene which process employs an adsorbent comprising type X or type Y zeolite containing calcium at the exchangeable cationic sites. The process in one embodiment employs a countercurrent-flow fixed-bed flow system and includes the steps of maintaining at least three serially connected zones, an adsorption zone, a purification zone and a desorption zone, in a column of the adsorbent; contacting the feed stream with adsorbent in the adsorption zone to effect the adsorption of para-xylene; withdrawing from the adsorption zone a raffinate stream comprising ethylbenzene; contacting the adsorbent in the desorption zone with a desorbent material comprising toluene to effect the displacement of para-xylene from the adsorbent; withdrawing an extract stream comprising para-xylene from the desorption zone; and passing at least a portion of the raffinate stream to a separation means and therein separating desorbent material from ethylbenzene to produce an ethylbenzene product. The improvement resides in passing a portion of the ethylbenzene product into the adsorption zone to effect the displacement of desorbent material adsorbed by the adsorbent during a previous contacting of adsorbent with desorbent material in the desorption zone.

19 Claims, 1 Drawing Figure

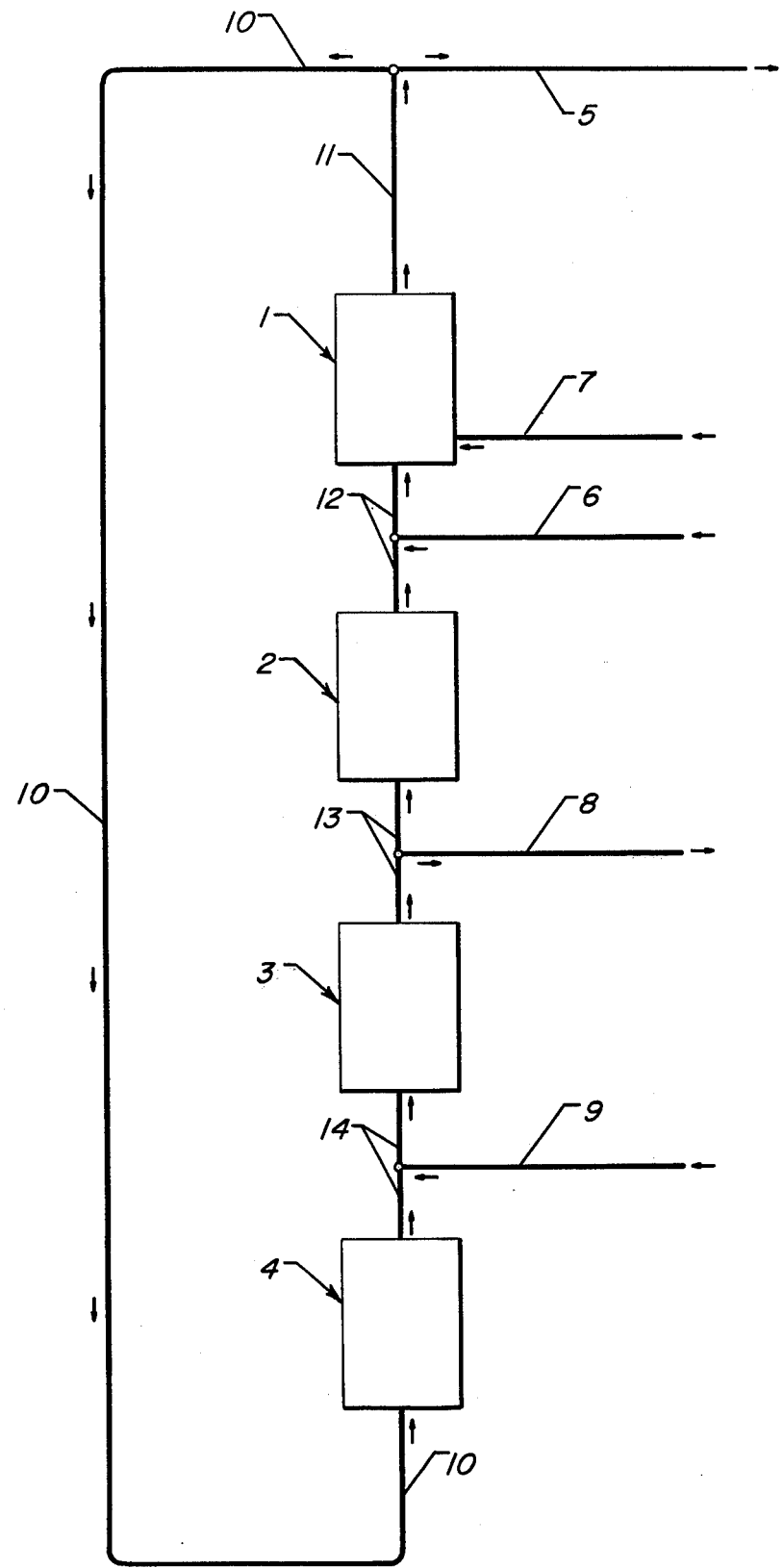

PROCESS FOR SEPARATING ETHYLBENZENE

BACKGROUND OF THE INVENTION

The field of art to which this invention pertains is hydrocarbon separation. More specifically the invention relates to an improved process for the separation of ethylbenzene from a feed stream comprising ethylbenzene and para-xylene which process employs a solid adsorbent comprising type X or type Y zeolite containing calcium at the exchangeable cationic sites which selectively removes the xylene isomer or isomers from the feed stream thereby producing a raffinate stream comprising ethylbenzene.

2. Description of the Prior Art

Applicant recognizes the abundance of prior art in the separation field especially that art relating to countercurrent fixed bed type operation which are commonly referred to as simulated countercurrent-flow fixed-bed type operations as particularly exemplified in U.S. Pat. No. 2,985,589.

Specific prior art patents which are considered closely related to the present invention are Broughton and Gerhold U.S. Pat. No. 2,985,589; Broughton U.S. Pat. No. 3,274,099; Pharis et al U.S. Pat. No. 3,732,325; Neuzil U.S. Pat. No. 3,696,107; Pharis et al U.S. Pat. No. 3,723,302; Adams et al U.S. Pat. No. 3,733,261; and Broughton U.S. Pat. No. 3,715,409. All of these patents relate to simulated countercurrent solid-fluid separation processes in which an extract component of a feed stream is separated by selective adsorption on a particular adsorbent and subsequently recovered in a higher concentration than that in the feed stream as a product stream. In each process there are various zones representing quantities of adsorbent material in which individual operations are taking place. In each, at least three operational zones are utilized: an adsorption zone, a purification zone and a desorption zone. In the adsorption zone, the selectively adsorbed extract material and perhaps some contaminant materials are adsorbed while the less selectively retained raffinate materials generally remain in the interstitial void spaces surrounding the adsorbent. The basic operation taking place in the purification zone is the purification of the adsorbed extract materials present in the absorbent; the adsorbent in "passing" through the purification zone becomes more concentrated with the extract material and less concentrated with raffinate materials. In the desorption zone a desorbent material removes the adsorbed extract material from the adsorbent.

The first patent discloses the basic concept of a simulated countercurrent solid-fluid contacting process employing a fixed bed of solid adsorbent having moving input and output streams which allow a segregation of zones in which separate functions are taking place in order to separate a feed stream into a raffinate product component and an extract product component.

The second U.S. Pat. No. 3,274,099 includes the same basic processing steps as the first patent but also includes an additional input stream into the purification zone, which is located between the adsorption zone and the desorption zone. The input stream is a sweeping agent, a raffinate-type (that is, a material which is relatively unadsorbed by the adsorbent) compound having a boiling point to permit separation by distillation from the feed raffinate component, which is passed into the process to push raffinate material which is trapped in the interstitial void spaces between adsorbent particles in the purification zone back into an adsorption zone to prevent feed raffinate material from passing from the adsorption zone through the purification zone and into a desorption zone thereby contaminating an extract product with feed raffinate material. In one embodiment, the process of U.S. Pat. No. 3,274,099 is used to separate normal paraffins from isoparaffins.

U.S. Pat. No. 3,732,325 discloses a process which employs the same basic processing steps of the first patent and a particular adsorbent to separate aromatic hydrocarbons, particularly the $C_8$ aromatics. In the process described in that patent a purification stream which comprises extract material is passed into the purification zone. The extract material can be taken either from an extract outlet stream from the process or from extract material which has been separated from desorbent material in an extract stream fractionator. The purification stream containing the extract material displaces from the interstitial void spaces between the adsorbent particles any raffinate materials carried into the purification zone, removes feed contaminants adsorbed by the adsorbent and reduces the quantity of desorbent which normally surrounds the adsorbent particles in the zone when no purification stream is used.

U.S. Pat. No. 3,696,107 discloses a process for separating para-xylene from a feed stream containing a mixture of $C_8$ aromatics which employs the basic processing steps described in the first patent, a particular crystalline aluminosilicate adsorbent and a two-stage desorption operation in which a first desorbent stream contacts adsorbent in the desorption zone to effect the desorption of para-xylene from the adsorbent and a second desorbent stream contacts the adsorbent in the desorption zone to effect the pushing of desorbed para-xylenes from the interstitial void spaces between the adsorbent particles. One extract stream is withdrawn from the process.

In U.S. Pat. No. 3,723,302, which discloses a process for separating olefins from paraffins employing the basis processing steps described in the first patent and a particular adsorbent, a two-step desorption operation is again used. The process uses two desorbent materials both of which enter into the desorption zone. The first desorbent material contacts the adsorbent in the desorption zone and causes contaminants to be desorbed from the adsorbent while the second desorbent material is used to desorb the product olefins from the adsorbent contained in the same desorption zone. Two extract streams are withdrawn from the process, an extract contaminant outlet stream and an extract olefin outlet stream.

U.S. Pat. No. 3,733,261 also discloses a process for separating olefins from paraffins which employs the basis processing steps of the first patent mentioned. In that process one desorbent material is admitted in two places in the desorption zone and two extract streams are removed from the process, an extract contaminant stream containing aromatic contaminants and desorbent material and an extract olefin stream containing olefins and desorbent material.

U.S. Pat. No. 3,715,409 discloses a process for the separation of aromatic hydrocarbons which employs four zones and includes the steps of: passing an extract material input stream into the purification zone to effect the desorption and displacement of raffinate material; passing at least a portion of the raffinate output stream passing out of the adsorption zone into the buffer zone to effect desorption and displacement of desorbent material; and, passing a raffinate input stream into an adsorption zone to effect displacement of desorbent from the adsorbent in that zone.

In the process described in my assignee's U.S. Pat. No. 3,917,734 issued to A. J. deRosset, ethylbenzene is recovered in high purity from a feed mixture comprising ethylbenzene and xylene isomers. The process basically comprises contacting the feed mixture with an adsorbent comprising type X or type Y zeolites containing calcium at the exchangeable cationic sites, selectively adsorbing the xylene isomers, and thereafter recovering ethylbenzene as a raffinate component. The adsorbed xylenes may then be recovered, in one embodiment, by contacting the adsorbent with a desorbent material, preferably comprising toluene, thereby desorbing the xylenes and then withdrawing the desorbed xylenes from the adsorbent. In a preferred embodiment the adsorption and desorption are done continuously in a simulated moving-bed countercurrent-flow system, the operating principles and sequence of which are described in U.S. Pat. No. 2,985,589.

It has been discovered that when the feed mixture to this deRosset proesss includes para-xylene and when the preferred toluene desorbent material is employed the selectivity of that adsorbent is higher for the toluene desorbent material than it is for para-xylene. This results in the inability of that process to obtain high purity product and high yields simultaneously when the para-xylene concentration of the feed is about the same as or less than that of ethylbenzene. The process of my invention eliminates that problem thereby making separation of ethylbenzene from xylene isomers in both high purity (98% or greater, expressed as a percent of $C_8$ aromatics present) and high yields (95% or greater) possible for any ethylbenzene concentration in the feed.

Ethylbenzene, used as a raw material in the production of styrene monomer, is commercially produced from the alkylation of benzene with ethylene. The cost of and competing demands for necessary benzene and ethylene feed streams have, however, prompted new efforts to recover ethylbenzene from various $C_8$ aromatic feed streams which already contain ethylbenzene. Such feed streams for instance include $C_8$ aromatic extracts produced by a typical solvent extraction process for a pyrolysis gasoline or from a naphtha which has been reformed with a platinum-halogen-containing catalyst. Additionally, $C_8$ aromatic cuts of hydrogenated pyrolysis naphthas or reformates prepared by fractionation without solvent extraction contain varying amounts of ethylbenzene. The particular utility of the process of my invention therefore is that it offers a method for recovering ethylbenzene from a feed stream which already contains ethylbenzene.

Ethylbenzene can, of course, be separated from the xylene isomers by fractionation but because its boiling point is within about 4° F. of that of para-xylene, the fractionation can be achieved only with the more intricate super-fractionators. Typical ethylbenzene fractionators contain 300 to 400 actual trays and require about a 25—50 to 1 reflux to feed ratio. The process of my invention therefore offers a competitive alternative to the separation of ethylbenzene by superfractionation.

SUMMARY OF THE INVENTION

It is, accordingly, a broad objective of my invention to provide a process for the separation of high-purity ethylbenzene at high recoveries from a feed mixture comprising ethylbenzene and para-xylene. It is a further objective that my process shall apply to a feed mixture containing any concentration of ethylbenzene or para-xylene.

In brief summary my invention is in one embodiment an improved process for separating ethylbenzene from a feed stream containing ethylbenzene and para-xylene which process employs an adsorbent comprising type X or type Y zeolite containing calcium at the exchangeable cationic sites and comprises the steps of: (a) contacting the adsorbent with said feed at adsorption conditions to effect the selective adsorption of para-xylene by the adsorbent; (b) removing a raffinate stream comprising ethylbenzene from said adsorbent; (c) contacting said adsorbent with a desorbent material comprising toluene at desorption conditions to effect the desorption of para-xylene from said adsorbent; and, (d) removing from said adsorbent an extract stream comprising para-xylene, the improvement which comprises contacting the adsorbent which has previous contacted desorbent material with a portion of a raffinate stream substantially free of desorbent material to effect the displacement of desorbent material prior to again contacting the adsorbent with the feed stream.

In another embodiment my invention is a process for the separation of a feed stream comprising a mixture of ethylbenzene and para-xylene which process employs an adsorbent comprising type X or type Y zeolite containing calcium at the exchangeable cationic sites and comprises the steps of: (a) maintaining net fluid flow through a column of an adsorbent in a single direction, which column contains at least three zones having separate operational functions occurring therein and being serially interconnected with the terminal zones of said column connected to provide a continuous connection of said zones; (b) maintaining an adsorption zone in said column, said zone defined by the adsorbent located between a feed input stream at an upstream boundary of said zone and a raffinate output stream at a downstream boundary of said zone; (c) maintaining a purfication zone immediately upstream from said adsorption zone, said purfication zone defined by the adsorbent located between an extract output stream at an upstream boundary of said purification zone and said feed input stream at a downstream boundary of said purfication zone; (d) maintaining a desorption zone immediately upstream from said purfication zone, said desorption zone defined by the adsorbent located between a desorbent input stream at an upstream boundary of said zone and said extract output stream at a downstream boundary of said zone; (e) passing said feed stream into said adsorption zone at adsorption conditions to effect the selective adsorption of para-xylene by said adsorbent in said adsorption zone and withdrawing a raffinate system comprising ethylbenzene from said adsorption zone; (f) passing a desorbent material comprising toluene into said desorption zone at desorption conditions to effect the displacement of para-xylene from the adsorbent in said desorption zone, and the adsorption of at least a portion of said desorbent material; (g) withdrawing an extract stream comprising para-xylene and desorbent material from said desorption zone; (h) passing at least a portion of said raffinate stream to a separation means and therein separating at separation conditions ethylbenzene from said desorbent material to produce an ethylbenzene product substantially free of desorbent material; and, (i) periodically advancing through said column of adsorbent particles in a downstream direction with respect to fluid flow in said adsorption zone the feed input stream, raffinate output stream, desorbent input stream, and extract output stream to effect the shifting of zones through said mass of adsorbent and the production of extract and raffinate streams, wherein the improvement comprises passing a portion of said ethylbenzene product into said adsorption zone to effect the displacement of desorbent material adsorbed by the adsorbent during a previous contacting of said adsorbent with desorbent material in said desorption zone.

Other objects and embodiments of the present invention encompass details about feed mixtures, adsorbents, desorbent materials and operating conditions all of which are hereinafter disclosed in the following discussion of each of the facets of the present invention.

DESCRIPTION OF THE INVENTION

In order to gain a better understanding of the process of this invention, the following definitions of terms that are used throughout this specification are given.

The term "feed stream" indicates a stream in the process through which feed material passes to the adsorbent. A feed material comprises one or more extract components and one or more raffinate components.

An "extract component" is a compound or type of compound that is selectively adsorbed by the adsorbent while a "raffinate component" is a compound or type of compound that is relatively non-adsorbed. In this process, the xylene isomers are extract components and ethylbenzene is a raffinate component. The term "raffinate stream" or "raffinate output stream" means a stream through which most of the raffinate components are removed from the adsorbent. The composition of the raffinate stream can vary essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high purity ethylbenzene at high recoveries, it will be appreciated that an extract component is never completely recovered, nor is a raffinate component completely non-adsorbed by the adsorbent. Therefore, small amounts of a raffinate component can appear in the extract stream and, likewise, small amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of an adsorbed xylene isomer to that of the non-adsorbed ethylbenzene will be lowest in the raffinate stream, next highest in the feed mixture, and the highest in the extract stream. Likewise, the ratio of the concentration of the non-adsorbed ethylbenzene to that of an adsorbed xylene isomer will be highest in the raffinate stream, next highest in the feed mixture, and the lowest in the extract stream.

The term "desorbent material" shall mean generally a material capable of desorbing an extract component or a raffinate component. The term "desorbent stream" or "desorbent input stream" indicates the stream through which desorbent material passes to the adsorbent.

The term "selective pore volume" of the adsorbent is defined as the volume of the adsorbent which selectively adsorbs extract components from the feed stock. The term "non-selective void volume" of the adsorbent is the volume of the adsorbent which does not selectively retain extract components from the feed stock. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent.

When adsorbent "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller that the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components.

The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed mixtures which can be utilized in the process of this invention will comprise ethylbenzene and at least one xylene isomer. Mixtures containing substantial quantities of ethylbenzene and the xylene isomers generally are produced by reforming and isomerization processes, processes which are well known to the refining and petrochemical arts.

In reforming processes, a naphtha feed is contacted with a platinum-halogen-containing catalyst at severities selected to produce an effluent containing $C_8$ aromatic isomers. Generally the reformate is then fractionated to concentrate the $C_8$ aromatic isomers in a $C_8$ fraction which may then be further concentrated by solvent extraction processes.

Xylene isomerization processes isomerize at isomerization conditions a xylene mixture which is deficient in one or more isomers to produce an effluent containing approximately equilibrium quantities of the $C_8$ aromatic isomers along with small quantities of $C_8$ non-aromatics. The equilibrium compositions of the xylene isomers and ethylbenzene at various temperatures are shown in Table 1 below.

Table 1

| Equilibrium $C_8$ Aromatic Compositions* | | | |
|---|---|---|---|
| Temperature, °C. | 327 | 427 | 527 |
| Mole Percent of $C_8$ aromatic isomers | | | |
| Ethylbenzene | 6 | 8 | 11 |
| Para-xylene | 22 | 22 | 21 |
| Meta-xylene | 50 | 48 | 45 |
| Ortho-xylene | 22 | 22 | 23 |

*Base on API sources

Feedstreams from which one or more $C_8$ aromatic isomers can be separated are, generally speaking, either extracted or non-extracted. An extracted feedstream is an extract product stream which has been produced by a typical solvent extraction process from a feed mixture containing both $C_8$ aromatic isomers and $C_8$ non-aromatics. The particular solvent selectively extracts the $C_8$ aromatics and an extract product essentially free of non-aromatics is produced. Non-extracted feedstreams are those containing both $C_8$ aromatic isomers and $C_8$ non-aromatics. Typically they are isomerates of $C_8$ fractions prepared by fractionating reformates or hydrogenated pyrolysis naphthas. Shown in Table No. 2 is an analysis of a typical non-extracted reformate $C_8$ heartcut in which the total $C_8$ non-aromatics, paraffins and monocycloparaffins, are 26.6 wt. %.

Table No. 2

| Typical Non-Extracted Reformate $C_8$ Heartcut Analysis M.S. Hydrocarbon Breakdown, Wt. % | |
|---|---|
| Aromatics | |
| $C_8$ | 73.2 |
| $C_9$ | 0.3 |
| | 73.5 |
| Paraffins | |
| $C_6$ | 0.1 |
| $C_7$ | 0.2 |
| $C_8$ | 2.1 |
| $C_9$ | 20.7 |
| $C_{10}$ | 0.8 |
| | 23.9 |
| Monocycloparaffins | |
| $C_6$ | 1.0 |
| $C_7$ | 1.2 |
| $C_8$ | 0.2 |
| $C_9$ | 0.2 |
| | 2.6 |

Likewise the effluent from a catalytic xylene isomerization process also contains varying amounts of these $C_8$ non-aromatics. Table No. 3 shows the amounts of individual $C_8$ non-aromatics contained in a typical isomerate. Here is the total $C_8$ non-aromatics amount to 8.52%.

Table No. 3

| Individual $C_8$ Non-Aromatic Components in a Typical Xylene Isomerization Reactor Effluent | |
|---|---|
| $C_8$ Paraffins | Wt. % In Reactor Effluent |
| 2,4-dimethylhexane | 0.33 |
| 2,3-dimethylhexane | 0.33 |
| 2-methylheptane | 0.63 |
| 4-methylheptane | 0.90 |
| n-octane | 0.33 |
| | 2.52 |
| $C_8$ Naphthenes | |
| 1,1,3-trimethylcyclopentane | 0.42 |
| 1,trans-2,cis-4-trimethylcyclopentane | .48 |
| 1,-trans-2,cis-3-trimethylcyclopentane | .12 |
| 1,1,2-trimethylcyclopentane | .18 |
| 1,cis-2,trans-4-trimethylcyclopentane | .12 |
| 1,cis-2,trans-3-trimethylcyclopentane | .12 |

Table No. 3-continued

| Individual $C_8$ Non-Aromatic Components in a Typical Xylene Isomerization Reactor Effluent | |
|---|---|
| 1,1-dimethylcyclohexane | .36 |
| 1,trans-4-dimethylcyclohexane 1,cis-3-dimethylcyclohexane | .90 |
| 1-methyl,cis-3-ethylcyclopentane | .42 |
| 1-methyl,trans-3-ethylcyclopentane 1-methyl,trans-2-ethylcyclopentane 1-methyl,4-ethylcyclopentane | 1.02 |
| 1,cis-2,cis-3-trimethylcyclopentane 1,trans-2-dimethylcyclohexane | .30 |
| 1,trans-3-dimethylcyclohexane 1,cis-4-dimethylcyclohexane | .42 |
| isopropylcyclopentane | .24 |
| 1-methyl,cis-2-ethylcyclopentane | .12 |
| 1,cis-2-dimethylcyclohexane | .12 |
| ethylcyclohexane | .66 |
| | 6.00 |

In the process of this invention all non-adsorbed feed components will appear in the raffinate stream along with ethylbenzene. Unless these components are later removed from the raffinate stream the purity of the ethylbenzene product will be reduced. It is therefore preferred that feedstreams to this process be extracted feedstreams although non-extracted feedstreams containing limited amounts of non-aromatics can also be used. Preferably such non-extracted feedstreams will contain less than about 10 vol. % non-aromatics.

Feedstreams to our process can also comprise effluent streams from processes which have removed varying amounts of one or more xylene isomers. As one example, at least a portion of the ortho-xylene may have been previously removed by fractionation from a feed mixture containing the xylene isomers. Ortho-xylene has a boiling point of about 5° F. higher than that of the nearest other $C_8$ aromatic (meta-xylene) and hence can be removed as a bottoms product from ortho-xylene fractionator towers. Such towers will typically contain about 100 to 105 actual trays and will operate with about a 5–8 to 1 reflux to feed ratio. The concentration of ortho-xylene in the effluent or overhead from this fractionation process which can be used as a feedstream to our process may then be less than the concentrations of either para-xylene. Alternatively a portion of the para-xylene may have been previously removed from a feed mixture containing the xylene isomers by a fractional crystallization process or by a solid-bed selective adsorptive process or by a combination of both. In this situation, the concentration of para-xylene in the effluent which is now charged as a feed stream to our process may then be less than the concentrations of either ortho-xylene or meta-xylene. As another alternative, perhaps at least a portion of both ortho- and para-xylene will have been previously removed, by the processes described above, from a feed mixture containing the xylene isomers. The concentration of both ortho-xylene and para-xylene in this feedstream to our process may then each be less than that of meta-xylene.

Desorbent materials used in various adsorptive separation process vary depending upon such factors as the type of operation employed. In the swing-bed system in which the selectively adsorbed feed component is removed from the adsorbent by a purge stream desorbent selection is not as critical and desorbent materials comprising gaseous hydrocarbons such as methane, ethane, etc., or other types of gases such as nitrogen or hydrogen may be used at elevated temperatures or reduced pressures to both to effectively purge the adsorbed feed component from the adsorbent.

However, in adsorptive separation processes which employ zeolitic adsorbents and which are generally operated at substantially constant pressures and temperatures to insure liquid phase, the desorbent material relied upon must be judiciously selected to satisfy, hopefully, all of several criteria. First, the desorbent material should displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component. Desorbent materials materials to be used in the process of this invention should additionally be substances which are easily separable from the feed mixture that is passed into the process. Both the raffinate stream and the extract stream are removed from the adsorbent in admixture with desorbent material and without a method of separating desorbent material, such as distillation, the purity of the extract components and the raffinate component would not be very high, nor would the desorbent material be available for reuse in the process. It is therefore contemplated that any desorbent material will have an average boiling point different than that of the feed mixture to permit separation therefrom by distillation. The boiling range of the desorbent material may be higher or lower than that of the feed mixture. Finally, desorbent materials should preferably be materials which are readily available, reasonable in cost and non-corrosive.

The prior art has recognized that desorbent materials comprising certain aromatic hydrocarbons most closely meet these criteria and are particularly effective for use in processes employed to separate $C_8$ aromatics. Specifically, desorbent materials comprising toluene are especially preferred for use in this process. Mixtures of toluene with paraffins are also effective as desorbent materials. Such paraffins must also be compatible with the adsorbent and feed mixture as described above and must be easily separable from the feed mixture. The paraffins can include straight or branched chain paraffins or cycloparaffins which meet these criteria. Typical concentrations of toluene in such mixtures can be from a few volume percent up to near 100 vol. % of the total desorbent material mixture but such concentrations preferably will be within the range of from about 50 vol. % to about 100 vol. % of the mixture.

It has also been recognized that certain characteristics of adsorbents are highly desirable, if not absolutely necessary to the successful operation of a selective adsorption process. Among such characteristics are: adsorptive capacity for some volume of an extract component per volume of adsorbent; the selective adsorption of extract components with respect to a raffinate component and the desorbent material; and sufficiently fast rates of adsorption and desorption of the extract components to and from the adsorbent.

Capacity of the adsorbent for adsorbing a specific volume of one or more extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent process adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

Equation 1

$$\text{selectivity} = (B) = \frac{[\text{vol. percent C/vol. percent D}]_A}{[\text{vol. percent C/vol. percent D}]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate the component D is preferentially adsorbed leaving an unadsorbed phase richer in component C and an adsorbed phase richer in component D. Ideally desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a non-adsorbed paraffinic tracer (n-nonane for instance) and of the particular $C_8$ aromatic isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the chromatographic traces, adsorbent performance can be rated in terms of capacity index for an extract component, selectivity for one isomer with respect to the other, and the rate of desorption of extract component by the desorbent. The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in Broughton U.S. Pat. No. 2,986,589. A specific laboratory-size apparatus utilizing these principles is described in deRosset et al U.S. Patent 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, California, Mar. 28 through Apr. 2, 1971.

Adsorbents to be used in the process of this invention will comprise specific crystalline aluminosilicates or molecular sieves. Particular crystalline aluminosilicates encompassed by the present invention include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when normal paraffin molecules are separated from isoparaffin molecules by using a particular molecular sieve. In the process of this invention, however, the term "molecular sieves" although widely used is not strictly suitable since the separation of specific $C_8$ aromatic isomers is dependent on differences in electrochemical attraction of the different isomers and the adsorbent rather than on pure physical size differences in the isomer molecules.

In hydrated form, the crystalline aluminosilicates generally encompass those zeolites represented by the Formula 1 below:

Formula 1

$$M_{2/n}O:Al_2O_3:wSiO_2:yH_2O$$

where "M" is a cation which balances the electrovalence of the tetrahedra and is generally referred to as an exchangeable cationic site, "$n$" represents the valence of the cation, "$w$" represents the moles of $SiO_2$, and "$y$" represents the moles of water. The cation "M" may be one or more of a number of possible cations.

The prior art has generally recognized that adsorbents comprising the type X and the type Y zeolites can be used in certain adsorptive separation processes.

These zeolites are described and defined in U.S. Pat. Nos. 2,882,244 and 3,120,007 respectively. As the type X and type Y zeolites are initially prepared, the cation "M" is usually predominately sodium and the zeolites are therefore referred to as sodium-type X zeolites and sodium-type Y zeolites respectively. Depending upon the purity of the reactants used to make the zeolites, other cations may be present as impurities.

Cations occupying exchangeable cationic sites in the zeolite may be replaced with other cations by ion exchange methods generally known to those having ordinary skill in the field of crystalline aluminosilicates. Such methods are generally performed by contacting the zeolite with an aqueous solution of the soluble salt of the cation or cations desired to be placed upon the zeolite. After the desired degree of exchange takes place the sieves are removed from the aqueous solution, washed, and dried to a desired water content. By such methods the sodium cations and any non-sodium cations which might be occupying exchangeable sites as impurities in a sodium-type X or sodium-type Y zeolite can be partially or essentially completely replaced with other cations.

Adsorbents which have been found to possess the characteristics described above and which are suitable for use in the process of separating ethylbenzene as a raffinate component are those comprising calcium-type X zeolite or calcium-type Y zeolite. Suitable adsorbents can be prepared by ion exchanging sodium-form type X or type Y zeolites to the desired calcium content. A zeolite commercially available from the Linde Company, Tonawanda, New York, under the trade name "Molecular Sieves 13X" can, for instance, be ion exchanged to produce a suitable calcium-containing zeolitic adsorbent. Particularly suitable for use as an adsorbent in the process of this invention is the calcium-containing type X zeolite also available commercially from the same company under the trade name "Molecular Sieves 10X". The calcium content of the type X or type Y zeolite used as adsorbents in this process will preferably be from about 2 to about 15 wt. % calcium and more preferably will be from about 9 1 to about 15 wt. % calcium.

Adsorbent content has also been found to be necessary to maintain optimum adsorbent performance. The preferred water content of the adsorbent used in this process will be from about 0.2 to about 4 wt. % water measured by loss on ignition at 500° C. This amount of water may be maintained if necessary by adding water to the adsorbent either on an intermittent or more preferably on a continuous basis by itself or in admixture with feed or desorbent material to maintain the desired concentrations of water on the adsorbent.

The adsorbent may be employed in the form of a dense compact fixed bed which is alternatively contacted with the feed mixture and desorbent materials. In the simplest embodiment of the invention the adsorbent is employed in the form of a single static bed in which case the process is only semi-continuous. In another embodiment a set of two or more static beds may be employed with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589. In such a system it is the progressive movement of multiple liquid access points down an adsorbent chamber that simulates the upward movement of adsorbent contained in the chamber. Generally four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of my process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the nonselective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is a downstream direction from the extract outlet stream to the feed inlet stream.

Immediately upstream of zone 2 with respect to the fluid flowing in zone 2 is the desorption zone or zone 3.

The desorption zone is defined as the adsorbent between the desorbent inlet and the extract outlet stream. The function of the desorption zone is to allow desorbent material which passes into this zone to displace the extract components which were adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams in the same direction as the overall fluid flow throughout the adsorbent bed, to allow a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input, raffinate product recycle and raffinate output streams pass are advanced in the same direction through the adsorbent bed. Both the manifold arrangement and disc valve are known in the art. Specifically rotary disc valves which can be utilized in this operation can be found in U.S. Pat. No. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain many series of individual beds being connected by connecting conduits upon which are placed input or output taps to which the various input or output streams can be attached and alternately and periodically shifted throughout the process to effect continuous operation. In some instances, the connecting conduits can be connected to transfer taps which during the normal operations do not function as a conduit through which material passes into or out of the process.

It is contemplated that at least a portion of the raffinate output stream will pass into a separation means wherein desorbent material can be separated to produce a raffinate product (ethylbenzene) substantially free of desorbent material. Additionally at least a portion of the extract output stream will preferably be passed to a separation means wherein desorbent material can be separated for reuse in the process and an extract product substantially free of desorbent material can be produced. The term "substantially free" shall mean that the concentration of desorbent material in either the extract product or the raffinate product shall be less than about 5 vol. % and more preferably less than about 1 vol. %. The separation means will typically be fractionation columns, the design and operation of which is well known to the separation art.

Reference can be made to the Description of the Drawing section of this specification, to D. B. Broughton U.S. Pat. No. 2,985,589, and to a paper entitled "Continuous Adsorptive Processing -- A New Separation Technique" by D. B. Broughton presented at the 34th Annual Meeting of the Society of Chemical Engineers at Tokyo, Japan on Apr. 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of ethylbenzene product that can be obtained with liquid-phase operation over those obtained with vapor-phase operation. Adsorption conditions will include a temperature range of from 40° C. to about 250° C. and a pressure range of from about atmospheric to about 500 psig to insure liquid phase. Desorption conditions will include the same range of temperatures and pressures as used for adsorption conditions.

The size of the units which can utilize the process of this invention can vary anywhere from those of pilot-plant scale (see for example my assignee's U.S. Pat. No. 3,706,812) to those of commercial design and can range in flow rates from as little as a few cc an hour up to many thousands of gallons per hour.

It has been discovered that when an adsorbent containing calcium-type X or calcium-type Y zeolite and a desorbent material containing toluene are used to separate ethylbenzene as a raffinate component from a feed mixture containing ethylbenzene and para-xylene that both high yields and high product purity cannot be obtained simultaneously, particularly when the paraxylene concentration of the feed is about the same or greater than that of ethylbenzene. The reason for this is because of the selectivities of the particular adsorbent for the individual xylene isomers and for toluene with respect to ethylbenzene. Typical selectivities for the three xylene isomers (p, m and o) and toluene with respect to ethylbenzene (e) for a calcium-type X zeolite are shown in Table 4.

Table 4

| Xylene and Toluene Selectivities for Ca-Type X Adsorbent | |
|---|---|
| p/e | 2.27 |
| m/e | 3.57 |
| o/e | 2.97 |
| toluene/e | 2.61 |

The data shows that the toluene/e selectivity is higher than the p/e selectivity but is less than either the m/e or the o/e selectivity. Since the adsorbent is more selective for toluene than for para-xylene, para-xylene does not get as easily and completely adsorbed as do meta- and ortho-xylene, particularly when the concentration of para-xylene in the feed stream is relatively high. The result is that high ethylbenzene purity and high recovery of ethylbenzenes cannot be obtained at the same time; process operating conditions can be changed somewhat to obtain either high purity or high recovery but at the expense of the other.

In the process of my invention a portion of the ethylbenzene product is passed to the adsorption zone to remove the more tightly adsorbed toluene desorbent material from the selective pore volume of the adsorbent thereby aiding the adsorption of the more weakly adsorbed para-xylene and thus making separation of ethylbenzene in high purity and at high recovery possible from a variety of possible feeds including those in which the para-xylene concentration is greater than or about the same as that of ethylbenzene. Since the purpose of passing ethylbenzene product to the adsorption zone is to displace desorbent material, the ethylbenzene product admitted to that zone should be substantially free of desorbent material. Typically the ethylbenzene product will be recycled to the adsorption zone from the raffinate output stream fractionation column. Preferably the ethylbenzene product will enter the adsorption zone closer to the feed input stream than to the raffinate output stream so that the ethylbenzene can flow through most of the length of the adsorption zone and perform its function. The amount of ethylbenzene recycled to the adsorption zone will depend upon such factors as the feed rate to the process and the concentration of para-xylene and ethylbenzene in the feed stream. Typically, the ethylbenzene recycle rate will be from about 5 to about 75 percent of the raffinate output stream rate with from about 5 to about 25 percent being a more preferred range.

DESCRIPTION OF THE DRAWING

The attached drawing illustrates one embodiment of the process of this invention. Briefly the drawing shows four separate operating zones, adsorption zone 1, purification zone 2, desorption zone 3 and optional buffer zone 4; connecting conduits 10, 11, 12, 13 and 14; input streams 6, 7, and 9 and output streams 5 and 8. The four zones as shown in the drawing are stationary beds of solid adsorbent particles but may in other instances consist of a series of one or more individual chambers connected in a serial manner. Each of the individual zones may be a single chamber or a series of beds stacked upon one another in a column making up a zone. Thus in some instances each of the above zones would contain the same general quantity of adsorbent and have the same general physical dimensions, but in other instances some zones may require more adsorbent than other zones.

As the drawing shows, the overall net liquid flow is in a upward direction but in some instances a zone may be operating in a manner to allow flow of fluid for a certain period of time in a direction opposite to the overall net flow of fluid. The adsorbent particle flow can be considered to be in a downward direction to help in understanding the processing steps taking place in various zones. During normal fixedbed countercurrent operation the adsorbent material remains stationary and the individual adsorption, purification, desorption and buffer zones, as defined, are moved through the adsorbent by shifting various input and output streams in a unidirectional manner to allow fluid to flow in a countercurrent direction with respect to solid adsorbent and to continuously product extract and raffinate streams. In most instances the shifting of the input and output streams along the fixed bed of adsorbent is done simultaneously and in the same distance along the bed of adsorbent. In other instances, it is desired that two or more zonal functions take place in the adsorbent between two input and output streams before the input and output streams are shifted.

In accordance with the definition of the zones previously given, the adsorption zone 1 is the adsorbent material located between feed input stream 6 and raffinate stream output stream 5. Purification zone 2 is located immediately upstream from adsorption zone 1 and shares the feed input stream 6 as a common boundary with adsorption zone 1. Purification zone 2 is the adsorbent located between the extract outlet stream 8 and feed input stream 6. Immediately upstream from the purification zone 2 is desorption zone 3 which shares the extract outlet stream 8 as a common boundary with purification zone 2. Desorption zone 3 is the adsorbent between extract outlet stream 8 and desorbent inlet stream 9. Immediately upstream from desorption zone 3 is optional buffer zone 4 which shares the desorbent inlet stream 9 as a common boundary with desorption zone 3 and shares raffinate outlet stream 5 as a common boundary with purification zone 1. Optional zone 4 is the adsorbent located between desorbent inlet stream 9 and raffinate output stream 5.

Terminal zones 1 and 4 are connected by connecting conduits 10 and 11. The connecting conduits allow a portion of the fluid flowing out of zone 1 via line 11 to eventually flow via line 10 into zone 4 or zone 3 depending whether or not the optional zone is utilized, thereby allowing a closed-loop circulation of fluid. Lines 12, 13 and 14 are other connecting conduits connecting, respectively, zones 1 and 2, zones 2 and 3 and zones 3 and 4 to allow a continuous passage of fluid from one zone to and through all the other zones. Specifically, the material passing out of the adsorption zone 1 via line 11 can pass into line 5 or a portion of it may be diverted via line 10 to be passed eventually into buffer zone 4. Feed stock which passes into the process via line 6 passes through connecting conduit 12 and into the adsorption zone 1. In some instances a portion of the fluid material which passes out of purification zone 2 via line 12 may pass in admixture with feed material, entering the process via line 6, into adsorption zone 1. Line 13 is a connecting conduit which allows, in some instances, a portion of the fluid material withdrawn from desorption zone 3 via line 13 to bypass line 8 and pass via line 13 into purification zone 2. In a similar manner line 14 connects buffer zone 4 and desorption zone 3 and a portion of the fluid material leaving buffer zone 4 is allowed to pass out of that zone, to contact material passing into the process via desorbent input stream line 9 and to pass in admixture with desorbent through line 14 into the desorption zone 3. This allows a reduction in process desorbent requirements from external sources -- namely, desorbent input stream line 9. Line 10 can contain a pump or other fluid displacement means in order to induce flow in the process in a direction passing from line 11 through line 10 and into buffer zone 4.

Other pumps and valves located on the input and output lines and the lines which connect the various zones which control flow into, out of and through the process are not shown. It is presumed they could be located where necessary by one skilled in the art to induce and control proper fluid flow in the process. The input streams passing into the various zones can be connected to high pressure sources or pumping means in order to induce flow into the process and the streams which pass out of the process can be regulated by back pressure valves in order to maintain regulated pressure drops through the zones to induce fluid flow. In some instances unidirectional flow directing devices such as check valves can be located on the conduits between the various zones where a pump around circuit is not utilized.

The operations taking place in various zones shown in the drawing are as follows:

Essential operations taking place in zone 1 are the contacting of an adsorbent material with a feed stream and the selective adsorption of an extract component within the selective pore volume of the adsorbent. In this separation process the extract component is one or more xylene isomers and the raffinate component is ethylbenzene. A feed stream passes into the process via line 6, and since the overall general direction of fluid flow within that zone is in upward direction, passes through line 12 along with any material which may pass out of zone 2 via line 12 into zone 1.

As feed is passed into zone 1 an equal volume of raffinate stream material is displaced from zone 1 leaving that zone via line 11. A portion or all of the raffinate stream which passes through line 11 may be removed from the process via line 5 with any portion not removed passing through line 10 into either zone 3 or zone 4 depending upon whether or not optional zone 4 is used in the process. Raffinate output stream line 5 may be directed to a separation means such as a fractionation column (not shown) for separation of raffinate components from desorbent materials.

The adsorbent in zone 1 may be envisioned as moving in a direction countercurrent to the fluid flow in the zone. A simulated flow of solids occurs into and out of the adsorption zone when the zones are shifted during a portion of the entire cycle of operations. The adsorbent entering zone 1 comes from zone 3 or zone 4 depending upon whether or not optional zone 4 is used in the process. If optional zone 4 is not employed then the adsorbent leaving zone 3 and entering zone 1 will generally contain desorbent material present in both the non-selective void volumes and the selective void volumes. In instances where zone 4 is employed then a portion of the raffinate stream can be passed via line 10 into zone 4 to displace desorbent material from the non-selective void volumes present in the adsorbent particles in zone 4 into zone 3 via line 14. The adsorbent which then passes from the buffer zone 4 into the adsorption zone 1 contains for the most part desorbent material located within the adsorbent particle's selective pore volume which the extract material is required to desorb in zone 1. Ethylbenzene recycle enters zone 1 through line 7 and removes at least a portion of the desorbent material from the adsorbent selective pore volume prior to the contacting of the adsorbent with the feed input stream at the upstream portion of the adsorption zone. This feature aids the adsorption of para-xylene in zone 1. Although line 7 may be placed anywhere along the adsorbent material located in zone 1 from its most upstream location at feed input stream line 6 to its most downstream location at raffinate output stream line 5, it is preferred that line 7 may be located more closely contiguous to the feed input stream line 6 so that ethylbenzene recycle can flow through most of the length of zone 1 and perform its function.

The adsorbent, in passing through the adsorption zone 1 from its downstream boundary toward its upstream boundary with respect to fluid flow in that zone, adsorbs extract material from the feed input stream. As the adsorbent passes out of the adsorption zone it contains extract material and some raffinate material located within the selective pore volume of the adsorbent. The material present in the non-selective void volume of adsorbent is generally raffinate material with small portions of extract material from the feed stock which have not been adsorbed by the adsorbent. This adsorbent then passes into the purification zone 2 passing into that zone at its downstream boundary feed input stream line 6.

The function of purification zone 2 is to eliminate raffinate material from both the adsorbent's selective pore volume and the adsorbent's non-selective void volume so that the adsorbent leaving the purification zone via its upstream boundary (line 8) contains as little raffinate material as possible which would contaminate the extract product. A portion of the extract stream, a mixture of desorbent and extract material, passes into purification zone 2 from zone 3 via line 13 and displaces any raffinate material from the adsorbent's selective pore volume and sweeps displaced raffinate material and raffinate material from the adsorbent's non-selective pore volume upwardly in the rising fluid stream toward the raffinate outlet stream line 5.

The adsorbent which passes out of purification zone 2 passes into desorption zone 3 via that zone's downstream boundary, extract output stream line 8. The operation taking place in the desorption zone is essentially the removal of xylene isomers from the adsorbent. The removal is effected by contacting the adsorbent with a desorbent material capable of displacing xylene isomers from the selective pore volume of the adsorbent. The desorbent material passes into desorption zone 3 via desorbent input stream line 9 and conduit 14. At least a portion of the desorbed xylenes pass out of desorption zone 3 in admixture with desorbent material via extract output stream line 8. Extract output stream line 8 will then pass to a separation means, typically a fractionation column (not shown), where xylene isomers will be separated from desorbent material. The adsorbent leaving desorption zone 3 contains desorbent material located at both the adsorbent's selective pore volume and non-selective void volume. The adsorbent then passes into optional buffer zone 4 entering zone 4 at its downstream boundary the desorbent material input stream line 9.

Optional zone 4 in this process can be used to both conserve the amount of desorbent used in the process and prevent the contamination of extract material by raffinate material components. When operational zone 4 is used, it is possible that a portion of the raffinate stream which does not pass out of line 5 can be passed into zone 4 via lines 10 and 11 to displace desorbent material from the non-selective void volume of the adsorbent particles in zone 4 and push desorbent material out of optional zone 4 via line 14 into zone 3. Since the desorbent material passes into the process via line 9 is connected to conduit 14 which connects optional zone 4 with desorption zone 3, the desorbent material which is displaced from the adsorbent in optional zone 4 tends to reduce the requirements of desorbent material which has to pass through line 9 into the process. The solid adsorbent leaving zone 4 at its upstream boundary the raffinate output stream line 5 contains essentially desorbent material in its selective pore volume with raffinate material present in the adsorbent's nonselective void volume.

In instances in which optional zone 4 is not utilized it is possible to pass some of the raffinate stream from zone 1 directly into zone 3. In such instances it is required that the composition of the material which leaves zone 1 via line 11 and which bypasses line 5 contains essentially no raffinate material. The initial raffinate material withdrawn from zone 1 contains a very high concentration of desorbent material and can be passed from lines 10 and 11 into zone 3. The flow of raffinate output stream leaving the process via line 5 may be stopped during this time. When the stream passing through lines 10 and 11 into zone 3 contains an appreciable quantity of raffinate material the flow into zone 3 via line 10 is stopped and the raffinate output stream is then withdrawn via line 5. While the raffinate materials are being withdrawn through line 5, an outside source of desorbent material can be passed into zone 3 via lines 9 or 10.

The input and output lines 5, 6, 7, 8 and 9 during normal operations carry the respective streams as described previously. In order to allow a continuous operation, it is necessary that the individual input and output streams each be shifted in the same direction and in most instances at the same time. By shifting the input and output streams throughout the bed of adsorbent, together with requiring that the terminal zones (adsorption zone 1 and buffer zone 4) have a connecting conduit, it is possible to continuously effect the individual operations taking place in the various zones. When the zones described above are being shifted by incremental amounts through stationary adsorbent material the adsorbent contacts in the following order, the adsorption zone, the purification zone, the desorption zone and the buffer zone respectively.

I claim as my invention:

1. In a process for separating ethylbenzene from a feed stream comprising a mixture of ethylbenzene and para-xylene which process employs an adsorbent comprising type X or type Y zeolite containing calcium at the exchangeable cationic sites and comprises the steps of:
    a. contacting the adsorbent with said feed at adsorption conditions to effect the selective adsorption of para-xylene;
    b. removing a raffinate stream comprising ethylbenzene from said adsorbent;
    c. contacting said adsorbent with a desorbent material comprising toluene at desorption conditions to effect the desorption of para-xylene from the adsorbent; and,
    d. removing from the adsorbent an extract stream comprising para-xylene, THE IMPROVEMENT WHICH COMPRISES contacting the toluene containing adsorbent which has previously contacted desorbent material with a portion of ethylbenzene containing raffinate stream substantially free of desorbent material to effect the displacement of toluene prior to again contacting the adsorbent with the feed stream.

2. The process of claim 1 further characterized in that said feed stream contains ortho-xylene.

3. The process of claim 1 further characterized in that said feed stream contains meta-xylene.

4. The process of claim 1 further characterized in that said feed stream contains para-xylene and one other xylene isomer.

5. The process of claim 1 further characterized in that said feed stream contains para-xylene, meta-xylene and ortho-xylene.

6. The process of claim 1 further characterized in that said adsorbent comprises type X zeolite.

7. The process of claim 1 further characterized in that said adsorption conditions and desorption conditions include a temperature within the range of from about 20° to about 230° C. and a pressure within the range of from about atmospheric to about 500 psig.

8. In a process for the separation of ethylbenzene from a feed stream comprising a mixture of ethylbenzene and para-xylene which process employs an adsorbent comprising type X or type Y zeolite containing calcium at the exchangeable cationic sites and comprises the steps of:
    a. maintaining net fluid flow through a column of an adsorbent in a single direction, which column contains three zones having separate operational functions occurring therein and being serially interconnected with the terminal zones of said column connected to provide a continuous connection of said zones;
    b. maintaining an adsorption zone in said column, said zone defined by the adsorbent located between a feed input stream at an upstream boundary of said zone and a raffinate output stream at a downstream boundary of said zone;
    c. maintaining a purification zone immediately upstream from said adsorption zone, said purification zone defined by the adsorbent located between an extract output stream at an upstream boundary of said purification zone and said feed input stream at a downstream boundary of said purification zone;
    d. maintaining a desorption zone immediately upstream from said purification zone, said desorption zone defined by the adsorbent located between a desorbent input stream at an upstream boundary of said zone and said extract output stream at a downstream boundary of said zone;
    e. passing said feed stream into said adsorption zone at adsorption conditions to effect the selective adsorption of para-xylene by said adsorbent in said adsorption zone and withdrawing a raffinate stream comprising ethylbenzene from said adsorption zone;

f. passing a desorbent material comprising toluene into said desorption zone at desorption conditions to effect the displacement of para-xylene from the adsorbent in said desorption zone, and the adsorption of toluene by said adsorbent;

g. withdrawing an extract stream comprising para-xylene and desorbent material from said desorption zone;

h. passing at least a portion of said raffinate stream to a separation means and therein separating at separation conditions ethylbenzene from said desorbent material to produce an ethylbenzene product substantially free of desorbent material;

i. periodically advancing through said column of adsorbent particles in a downstream direction with respect to fluid flow in said adsorption zone the feed input stream, raffinate output stream, desorbent input stream, and extract output stream to effect the shifting of zones through said mass of adsorbent and the production of extract and raffinate streams, WHEREIN THE IMPROVEMENT COMPRISES passing a portion of said ethylbenzene product into said adsorption zone to effect the displacement of toluene adsorbed by the adsorbent during a previous contacting of said adsorbent with desorbent material in said desorption zone.

9. The process of claim 8 further characterized in that said feed stream contains ortho-xylene.

10. The process of claim 8 further characterized in that said feed stream contains meta-xylene.

11. The process of claim 8 further characterized in that said feed stream contains para-xylene and one other xylene isomer.

12. The process of claim 8 further characterized in that said feed stream contains para-xylene, meta-xylene and ortho-xylene.

13. The process of claim 8 further characterized in that said adsorbent comprises type X zeolite.

14. The process of claim 8 further characterized in that said adsorbent contains from about 2 to about 15 wt. % calcium.

15. The process of claim 8 further characterized in that said adsorbent contains from about 0.2 to 4 wt. % $H_2O$ measured by loss on ignition at 500° C.

16. The process of claim 8 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

17. The process of claim 8 further characterized in that it includes the step of passing at least a portion of said extract output stream to a separation means and therein separating at separation conditions desorbent material to produce an extract product substantially free of desorbent material.

18. The process of claim 8 further characterized in that said adsorption conditions and desorption conditions include a temperature within the range of from about 20° C. to about 230° C. and a pressure within the range of from about atmospheric to about 500 psig.

19. The process of claim 8 further characterized in that the ethylbenzene product passing into the adsorption zone enters the adsorption zone at a point closer to the feed input stream than to the raffinate output stream.

* * * * *